(12) United States Patent
Olsen et al.

(10) Patent No.: US 8,677,823 B2
(45) Date of Patent: Mar. 25, 2014

(54) ACOUSTIC THICKNESS MEASUREMENTS USING GAS AS A COUPLING MEDIUM

(75) Inventors: Age A. Olsen, Ingeberg (NO); Jostein Jacobsen, Lommedalen (NO); Tore Magne Halas Skar, Borgen (NO); Petter Norli, Oslo (NO); Ashild Bergh, Drammen (NO); Nils-Otto Negard, Vøyenenga (NO); Steinar Lag, Hvalstad (NO)

(73) Assignee: Halfwave AS, Hovik (NO)

( * ) Notice: Subject to any disclaimer, the term of this patent is extended or adjusted under 35 U.S.C. 154(b) by 693 days.

(21) Appl. No.: 13/006,478

(22) Filed: Jan. 14, 2011

(65) Prior Publication Data

US 2011/0106493 A1    May 5, 2011

Related U.S. Application Data

(63) Continuation of application No. 12/209,221, filed on Sep. 12, 2008, now Pat. No. 7,975,548.

(60) Provisional application No. 60/971,655, filed on Sep. 12, 2007.

(30) Foreign Application Priority Data

Sep. 12, 2007 (NO) .................................. 20074643

(51) Int. Cl.
*G01N 29/04* (2006.01)
(52) U.S. Cl.
USPC .................... 73/579; 73/597; 73/602; 73/659
(58) Field of Classification Search
USPC ............................. 73/579, 597, 598, 602, 659
See application file for complete search history.

(56) References Cited

U.S. PATENT DOCUMENTS 4,539,847 A * 9/1985 Paap ............................... 73/579
5,866,819 A * 2/1999 Albu et al. ...................... 73/629
(Continued)

FOREIGN PATENT DOCUMENTS

| JP | 9281087 | 10/1997 |
|---|---|---|
| SU | 504920 | 5/1976 |
| WO | 01/83122 | 11/2001 |

OTHER PUBLICATIONS

Mahesh C. Bhardwaj: "Non-contact ultrasound: The last frontier in non-destructive testing and evaluation", published on the world wide web page http://www.ultragroup.com/Company/Publications/PDF/esm1.pdf.

*Primary Examiner* — J M Saint Surin
(74) *Attorney, Agent, or Firm* — Young & Thompson (57) ABSTRACT

An acoustic apparatus adapted to operate in a gas filled space from a first side of an object to be measured for making a non-contact thickness measurement thereof includes an electro acoustic transducer, a transceiver coupled with the electro acoustic transducer and adapted to excite electro acoustic transducer to output an acoustic signal towards the object to be measured and receive an acoustic response signal therefrom, and a signal processor adapted to process the response signal and determine a thickness of the object. The electroacoustic transducer has a transducer-to-gas acoustic interface, and the transceiver is adapted to operate the electroacoustic transducer so as to emit into a gas filled gap an acoustic broad band pulse towards the object and to receive an acoustic resonance response signal in the acoustic response signal at a level that allows acquisition of the resonance response signal above a predetermined signal to noise level.

24 Claims, 9 Drawing Sheets

(56) References Cited

U.S. PATENT DOCUMENTS

| | | | |
|---|---|---|---|
| 5,974,886 A * | 11/1999 | Carroll et al. | 73/598 |
| 6,035,717 A * | 3/2000 | Carodiskey | 73/597 |
| 6,250,159 B1 | 6/2001 | Kreier et al. | |
| 6,363,787 B1 * | 4/2002 | Carlson et al. | 73/579 |
| 6,397,680 B1 * | 6/2002 | Levesque et al. | 73/602 |
| 7,757,561 B2 * | 7/2010 | Laugharn et al. | 73/644 |
| 2004/0032188 A1 | 2/2004 | Bhardwaj | |
| 2004/0100282 A1 | 5/2004 | Christensen et al. | |

* cited by examiner

FIG.11 ered by ref-
ACOUSTIC THICKNESS MEASUREMENTS USING GAS AS A COUPLING MEDIUM

CROSS REFERENCE TO RELATED APPLICATIONS

This application is a new continuation of co-pending application Ser. No. 12/209,221 filed on Sep. 12, 2008, which is a non-provisional application of the Provisional Application No. 60/971,655 filed on Sep. 12, 2007, and which claims priority to both Norwegian Application No. 2007 4643 filed on Sep. 12, 2007 and PCT Application No. PCT/NO2008/00318 filed on Sep. 9, 2008. The entire contents of each of the above-identified applications are hereby incorporated by reference.

BACKGROUND OF THE INVENTION

A. Available Gas Pipelines Monitoring System

Two main methods are available today for inspection/monitoring the status of the walls in gas pipe lines, namely, optical methods and methods known as Magnetic Flux Leakage methods. Typically it is of interest to be able to determine the pipe wall thickness and other conditions of the pipe during regular inspections, preferably under normal operating conditions, and without having to take special measures, such as e.g. filling the pipe with a liquid for the purpose of providing a coupling medium for performing such measurements by ultrasonic means, since such special measures are costly and cause long disruptions in the operation of the pipeline involved. Optical methods are such as the one utilized by the "Optopig", which is laser based and measures the distance to the wall with a resolution along and across the pipe wall of about 1 mm adapted to the inner surface, but does not measure the "remaining" thickness. The system is generally not applicable for areas covered by condensate or other liquid material. The Magnetic Flux Leakage method is a method which calculates the mass loss within a given area, but is not able to calculate absolute thicknesses, and the method is not applicable for very thick pipe walls.

It has long been stated that non-contact ultrasound (NCU) measurements of thickness and other characteristics of in a situation where a gas atmosphere exists between the measuring apparatus and the object to be measured generally is considered an impossible dream. In a pre-print of a chapter for "Encyclopedia of Smart Materials", editor A. Biederman, John Wiley & Sons, New York (expected in 2001), by Mahesh C. Bhardwaj, that general view is emphasised. While some techniques for making NCU measurements are suggested in the aforementioned publication, they all appear to suffer from limitations to the extent that their commercial application and success in the market have not become apparent to the present applicants for patent.

Accordingly, there is a need for an apparatus and method that is simple in use, and that reliably and accurately provides NCU measurements of thickness and other characteristics of an object to be measured in a wide range of applications, and in particular for applications such as gas pipeline inspections.

B. Field of Invention

The present invention is particularly suitable for simultaneously monitoring gas pipelines for corrosion and characterize the medium outside the pipe wall. More particularly, the present invention relates to a novel apparatus and method for the in situ monitoring of such gas pipes from the inside, and at the same time characterize the medium surrounding the pipe. If the pipe is coated, the characterization could be to decide whether the coating has loosened from the pipe wall or not. The method is also applicable with some geometric limitations if there is a liquid layer covering the bottom of the pipe, the geometric limitations relates to the critical angle between the gas medium and the water surface. Above the critical angle all acoustic energy is reflected from the surface, and measurements are not possible for angles larger than this critical angle. One and the same apparatus is also applicable within the range of known offshore and onshore pipeline diameters (up to about 1.50 m).

By insonifying the pipe wall with pulsed acoustic energy comprising components with wavelengths corresponding to twice the thickness of the wall, or integral numbers of this value, these frequencies will create standing waves across the pipe wall. When the emitted pulse comes to an end, resonant energy is reradiated, and detected by a receiving transducer located at a distance from the wall.

Figure 1A:
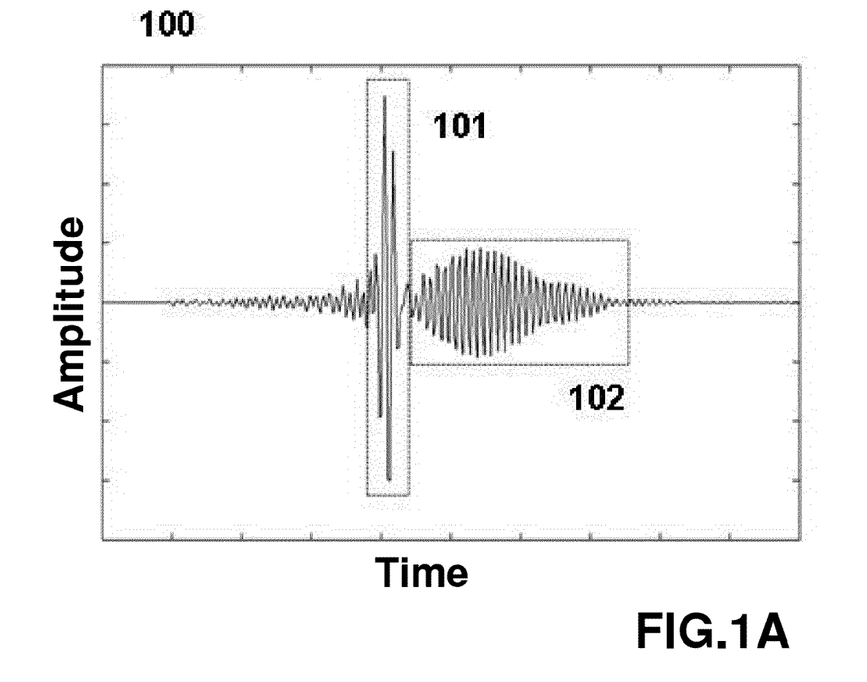
FIG. 1A-1B are schematic views of a pipe wall 110 where the media on each side of the wall are similar, and the resulting reflected signal 100 from this wall is also shown.
Figure 1B:
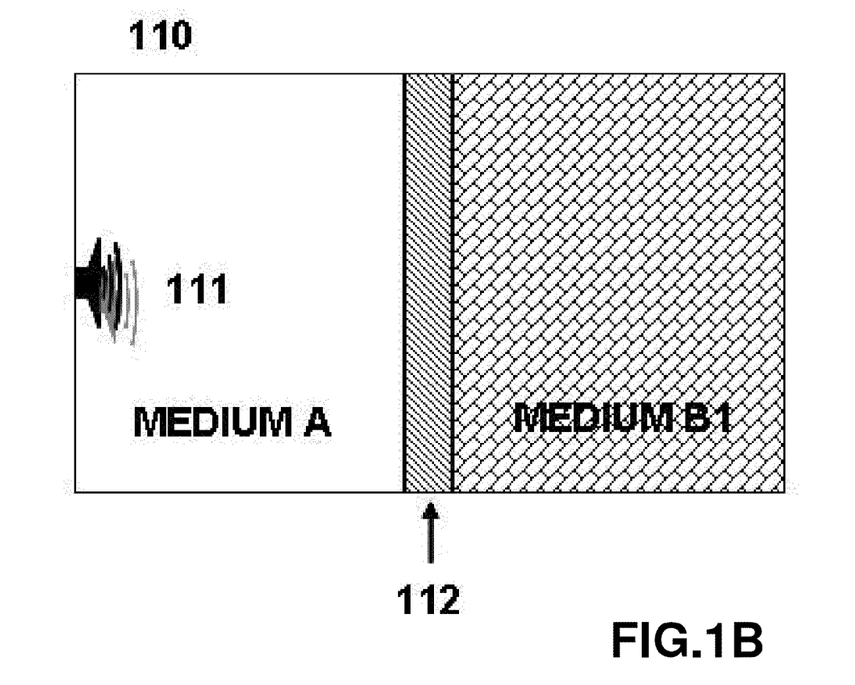

Referring to FIG. 1 this shows an example of an acoustic signal 100 emitted from a transducer 111, reflected by a steel pipe wall 112 and received by a receiver transducer 111. Inside the pipe is a medium A, and outside the pipe is a medium B1. The acoustic signal 100 is comprised of a direct reflected part 101 and a resonant part 102. The amount of energy contained in the received signal, is influenced by the acoustic characteristics of the pipe wall as well as by the media on both sides of the wall. The closer the acoustic impedance of the medium behind the wall is to the acoustic impedance of the wall, the lower is the total reflected energy.

Figure 2A:
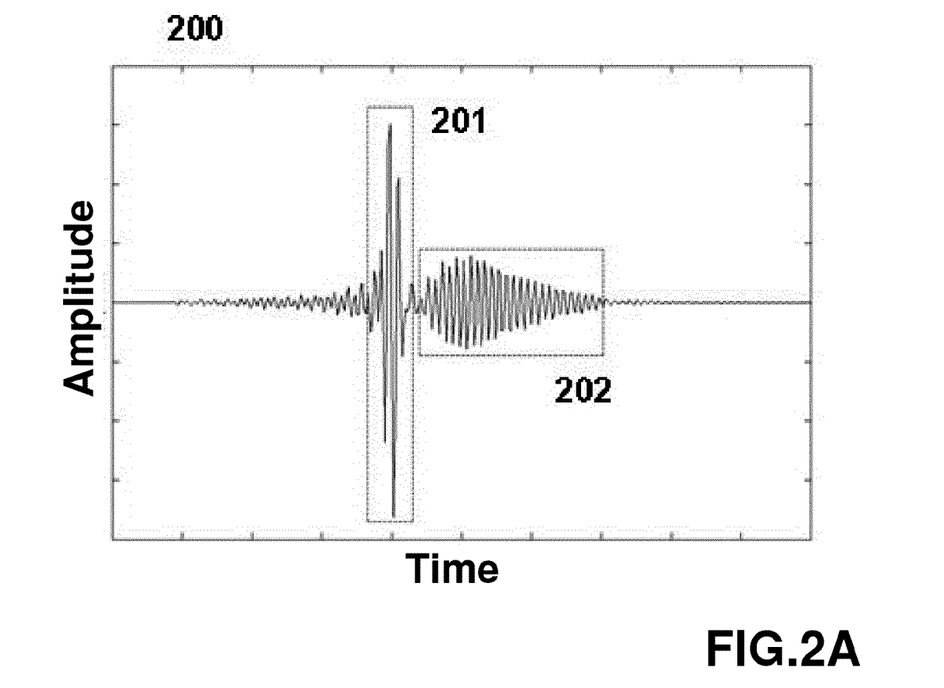
FIG. 2A-2B are schematic views of a pipe wall 210 where the medium inside and outside of the wall are different, and the resulting reflected signal 200 from this wall is also shown.
Figure 2B:
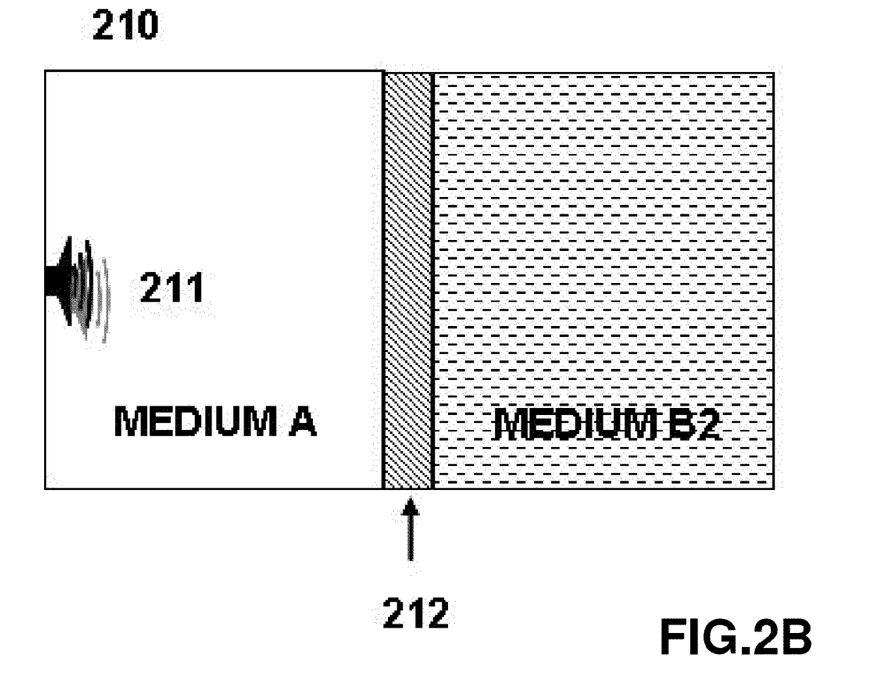

Referring to FIG. 2 this shows a corresponding result as in FIG. 1, only medium B2 is now different from medium B1 in FIG. 1, and as can be seen by comparing FIG. 1 and FIG. 2, the resonant part (102 and 202) of the reflected acoustic energy has changed.

SUMMARY OF THE INVENTION

The present invention provides an acoustic apparatus adapted to operate in a gas filled space and from a first side of an object to be measured for making a non-contact thickness measurement of the object to be measured or for making a non-contact characterisation of a medium located on a second side of the object to be measured. Advantageously, the apparatus of the invention is embodied as an electro acoustic. The apparatus typically comprises an electro acoustic transducer means,
a transceiver means coupled with the electro acoustic transducer means and adapted to excite the electro acoustic transducer means to output an acoustic signal towards the object to be measured and receive an acoustic response signal there from, and
a signal processor adapted to process the response signal and to determine on basis of the acoustic response signal a thickness characteristic of the object to be measured.

The electro acoustic transducer means of the invention has a transducer-to-gas acoustic interface, and the transceiver is adapted to operate the electro acoustic transducer means so as to emit into a gas filled gap between the electro acoustic transducer means and the object to be measured an acoustic broad band pulse towards the object and to receive the an acoustic resonance response signal in the acoustic response signal at a level that allows an acquisition of the resonance response signal above a predetermined signal to noise level. The signal processor is adapted to determine the thickness characteristic of the object to be measured or to make a characterisation of a medium located on a second side of the object to be measured using a fast Fourier transformation (FFT) of the acquired resonance response signal above the predetermined signal to noise level.

In an embodiment of the apparatus of the present invention, the transceiver means coupled with the electro acoustic transducer means is adapted to operate with acoustic signals having acoustic components in a frequency range that is at least a decade lower than frequencies used in time of flight thickness measurements of the object to be measured.

In a further embodiment of the apparatus of the present invention, it includes a transducer carrier means adapted to maintain the gas filled gap at a predetermined distance from a surface of the object facing the gas filled gap.

In a yet further embodiment of the apparatus of the present invention, the transducer carrier means is adapted to convey the electro acoustic transducer along the surface of the object facing the gas filled gap.

In a still further embodiment of the apparatus of the present invention, it is adapted to automatically establish the predetermined distance on basis of at least one of a nominal thickness of the object to be measured, acoustic characteristics of the gas in the gas filled gap, and frequencies of the broad band pulse, so as to optimise a quality of the non-contact thickness measurement.

The present invention represents increased value for pipe line inspection as it is able to measure from the inside of the at least partly gas filled pipe the absolute pipe wall thicknesses through a gas layer as a coupling medium for an acoustic signal, the gas layer now with the employment of the apparatus or method of the present invention is allowed to be in the range of less than or about 10 millimeters and up to 1000 millimeters or more, and simultaneously able to characterize the medium located outside the pipe wall. It is also applicable in gas pipe lines with condensate present, and one and the same apparatus is applicable for use in pipes of different diameters.

Further embodiments are readily understood from the following detailed description of the invention, and examples and the drawings used to explain and disclose the invention.

DETAILED DESCRIPTION OF THE EMBODIMENTS

With Respect to the Overall System of the Invention

Figure 3:
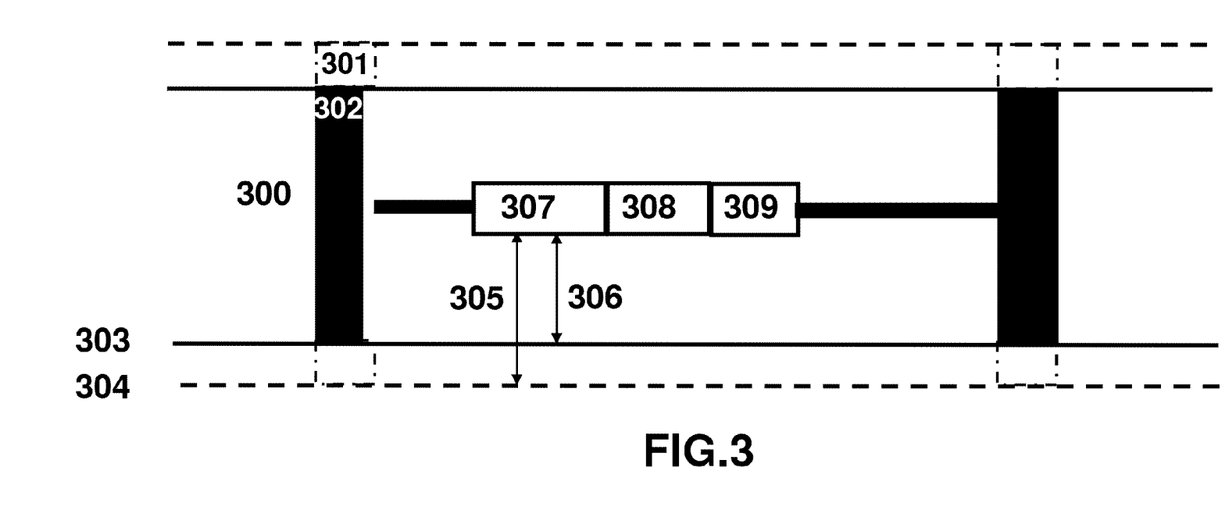
FIG. 3 is a schematic view of the system of invention applied for gas pipe line inspection.
Figure 4:
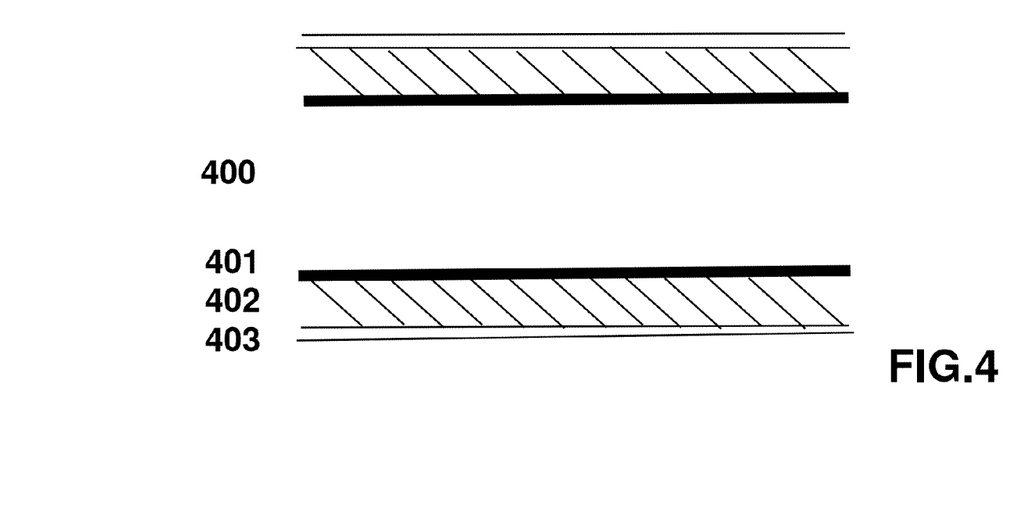
FIG. 4 is schematic view of a pipe with two coating layers.

Referring to FIG. 3, this shows a schematic of an example of a scenario depicting the use of the system according to the invention. A pipe is filled with gas 300 with pressure in the range from 1 bar and upwards, for example natural gas transported from a reservoir. The system of the invention employed in this scenario is preferably designed to map the complete thickness distribution of the pipe wall, and also characterize the medium/media surrounding the pipe. The distance between the transducers and the pipe wall can vary indicated by the arrows 305 and 306 in dependency of a variation of the diameter of the pipe. Inside the pipe is a carrier device 301 for a large diameter pipe and 302 for a smaller diameter pipe, preferably an off-the-shelf pig, housing the ultrasonic transducer array 307, and including the analog and digital electronics 307 and 308 and the power supply 309. The pig moves through the pipe driven by the gas flow. Referring to FIG. 4, the pipe 400 is typically made of steel walls 401, and may be covered by one or more coating layers 402 and 403. The task of characterizing the medium on the outside of the steel pipe wall could for example be to detect occurrences when the inner coating has loosened from the steel pipe wall.

With Respect to the Transducers

Figure 5:
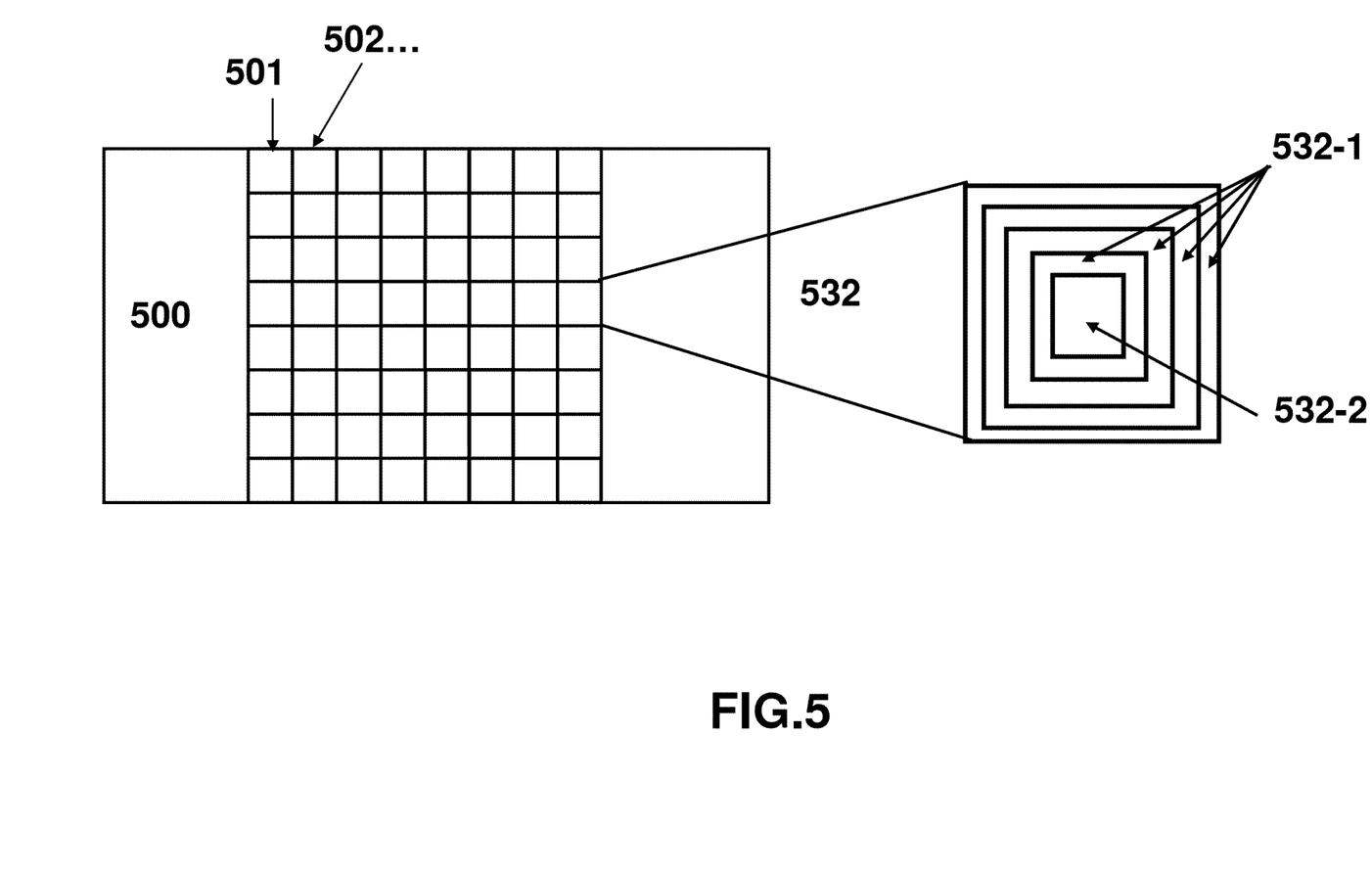
FIG. 5 is a schematic view of one possible design of a transducer module and of one single transducer.

Referring to FIG. 5, this shows a schematic of one half of a cylindrical transducer module 500, and one of the transducers 532 comprising a number of transmitting elements 532-1 and one receiving element 532-2. This design would be one of a number of possible designs. The transmitting transducer elements would typically be single crystal composites, while the receiving transducer elements would typically be piezocomposite elements. The transducer may advantageously have one or more matching layers in front of the transducer face (not shown in the figure) to improve the coupling of acoustic energy at the interface between the transducer and the gaseous medium due to the difference in acoustic impedance. Both the transmitting and the receiving elements will be inside a housing that contains the electrodes coupled to each of the transmitting and receiving elements. Typically the housing also has the contact for electrically connecting the transducer to the electronic part of the system.

Depending on the speed of the pig the transmitting and receiving part of the transducers could be spatially separated.

Figure 6:
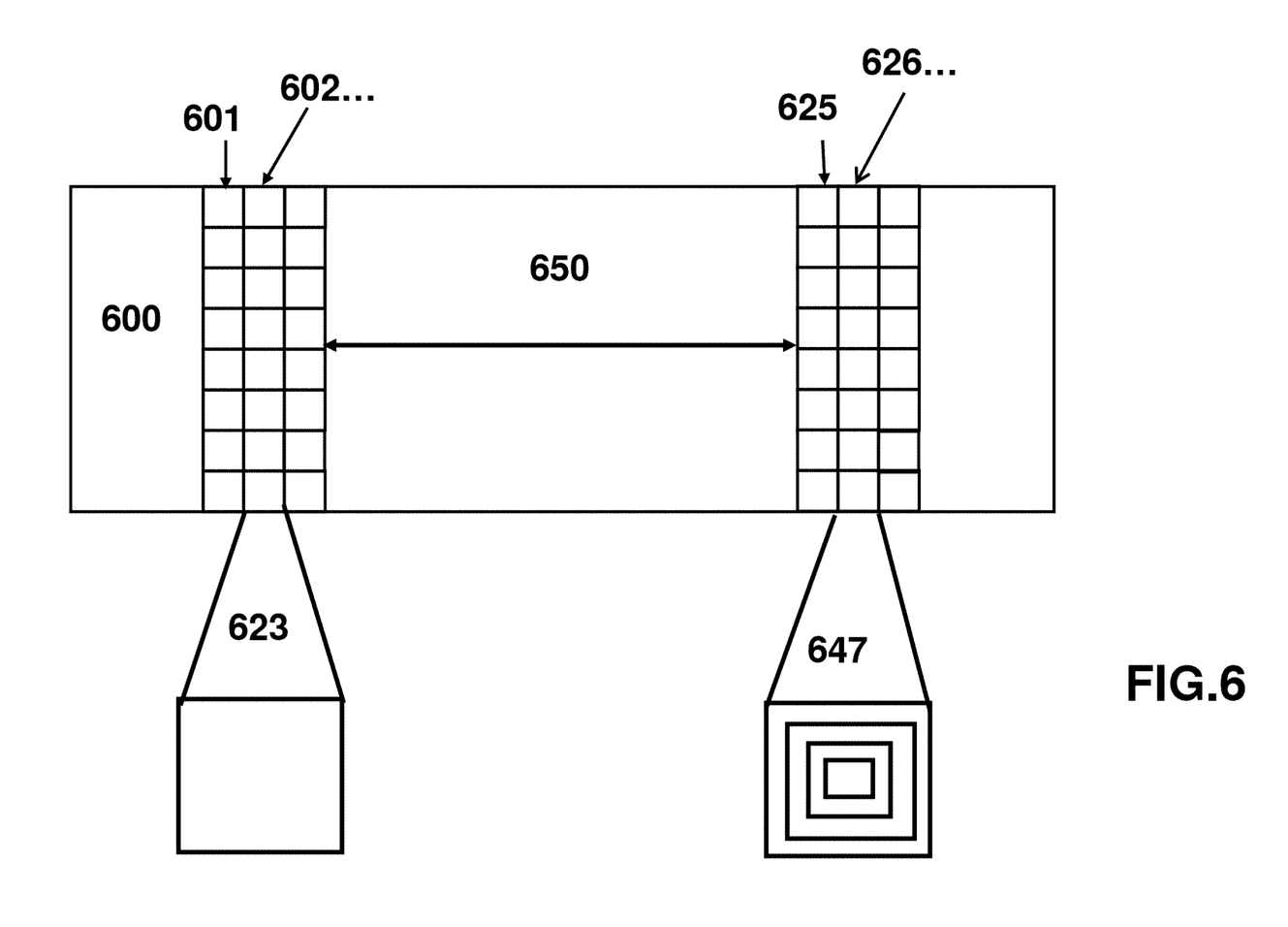
FIG. 6 is an outline of a design of a transducer module where the transmitting array are spatially separated from the receiving array.

Referring to FIG. 6, this shows an arrangement where the receiving transducer array 601-624 are spatially separated from the transmitting transducer array 625-648. Depicted in the figure are the gas pipe transducer module 600, the distance between the arrays 650, one element from the transmitting transducer array 647 as well as one element from the receiving transducer array 623. The design shown in FIG. 6 is only one of a number of possible designs.

Figure 7:
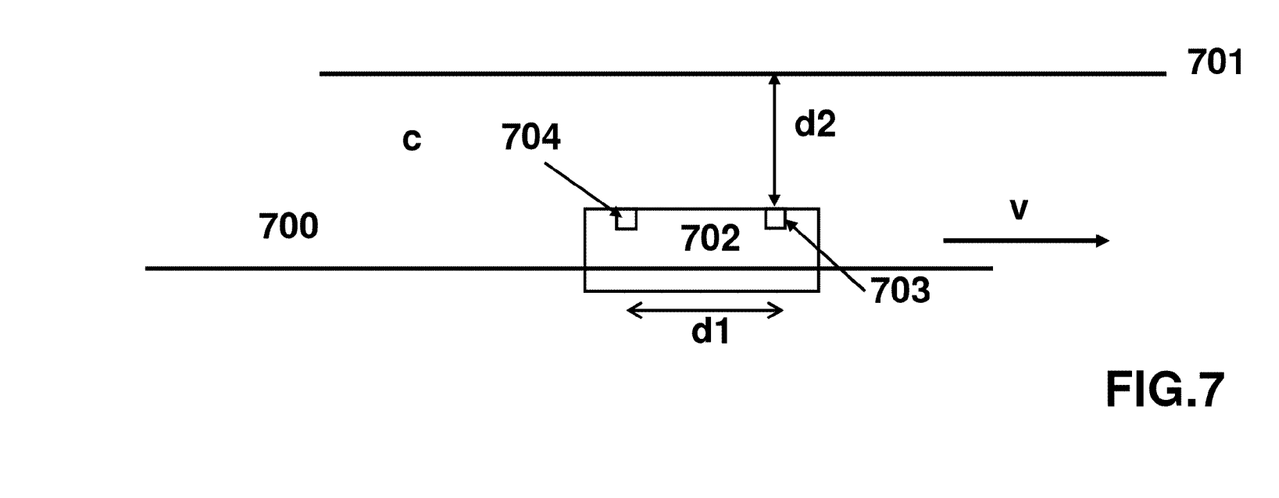
FIG. 7 is an outline of the transducer module in a pipe to illustrate how the distance between the corresponding transmitting and receiving transducers depends on velocities of gas and sound, and distance to the pipe wall.
Figure 8A:
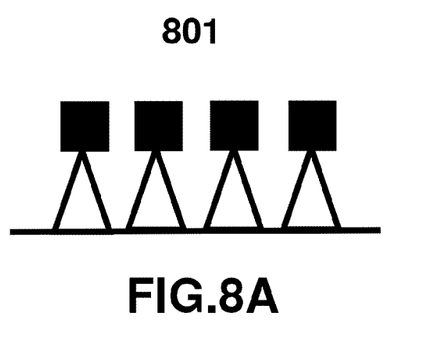
FIG. 8A-8F depict two arrays seen from different aspects.
Figure 8B:
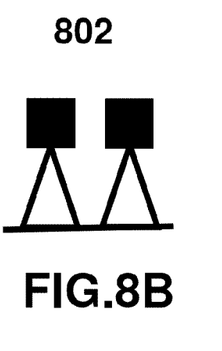
Figure 8C:
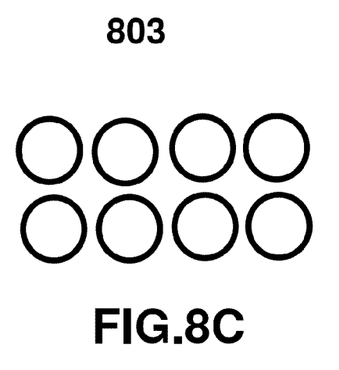
Figure 8D:
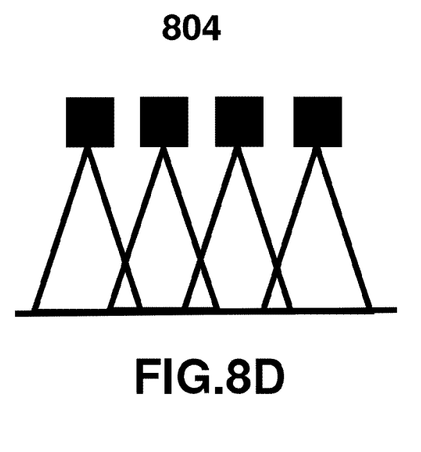
Figure 8E:
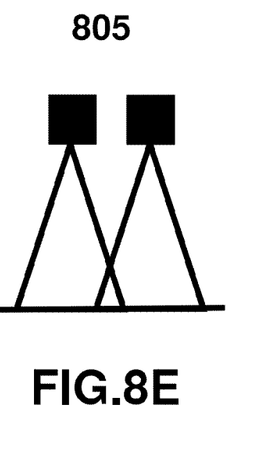
Figure 8F:
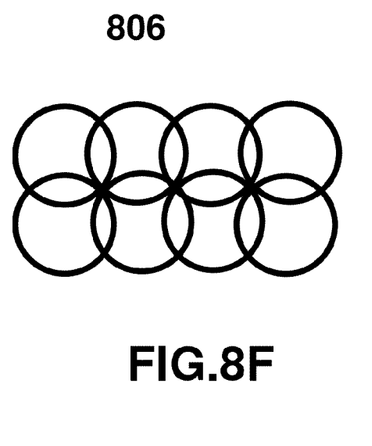

Referring to FIG. 7 a pipe 700 with steel pipe walls 701 and the transducer module 702 is shown. c is the speed of sound in the gas medium inside the pipe, and v is the velocity of which the carrier pig is moving. The distance d1 between the corresponding transmitting 703 and receiving transducers 704 depends on the velocity v of the gas, the sound velocity, c, and the distance from the transducer to the pipe wall d2 according to the formula:

$$d1 = (2 \cdot d2 \cdot v)/c$$

The apparatus of invention contain a mechanical arrangement to change the distance d1 according to the above formula.

The number of transducers will depend on the desirable coverage of the circumference of the pipe wall, while the transmitting frequency relative to the speed of the gas decide the coverage in the lateral direction. The transducers in the array could be operated individually or beam forming could be applied.

Referring to FIG. 8 depicting two arrays seen from two different aspects in 801 and 802, and in 804 and 805. To make the illustrations simple only a static example is depicted. 803 shows the resulting acoustical insonified areas (footprints) from each transducers of the array shown in 801 and 802. The coverage is less than 100%. Correspondingly the arrangement shown in 804 and 805 results in overlapping footprints and 100% coverage as shown in 806.

Figure 9:
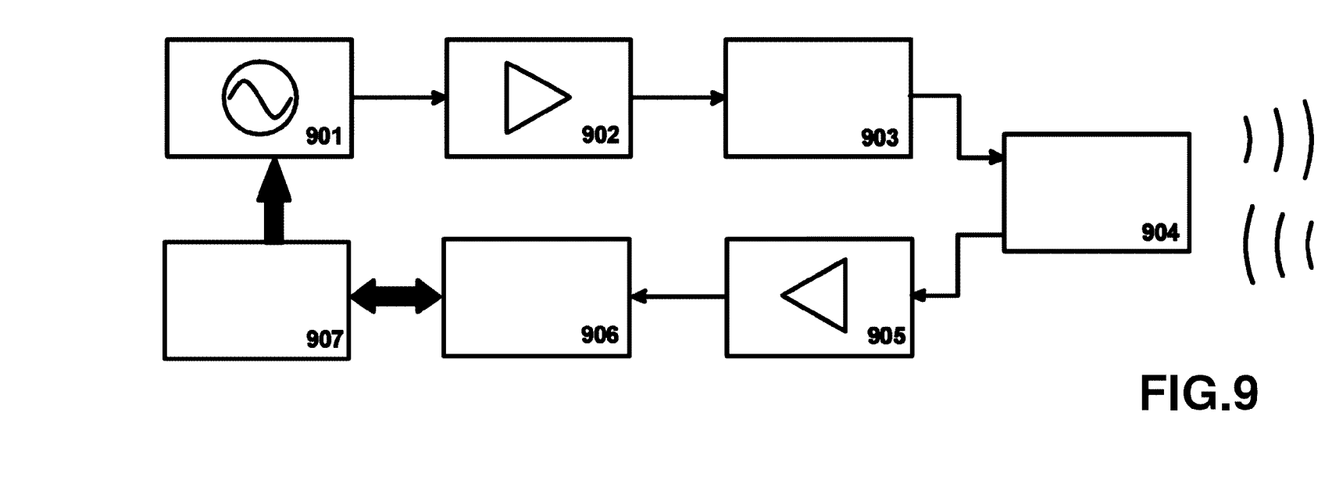
FIG. 9 is a schematic view of one possible design of the system for gas pipelines monitoring system.

With Respect to the Electronic System:

FIG. 9 shows a block diagram of the system shown in FIG. 3 used for in situ measurements of material properties of an object and the medium behind with a gaseous medium as the acoustic coupling medium used in the present invention.

A broadband electrical waveform is generated in a function generator 901. In order to get the best signal to noise ratio possible, the amplitude of the broadband electrical waveform is increased using a power amplifier 902. When gas is used as coupling medium between the transducers and the object, the transducers requires higher excitation voltages compared to transducers coupled to media having higher acoustic impedance as e.g. water, in order to have the same signal to noise ratio. This is due to the large mismatch in acoustic impedance between the gaseous media and the transducer, in addition to higher attenuation of acoustic energy in gas compared to e.g. water.

A transmitting matching network 903 is used to improve the system bandwidth. Such a matching network allows the power amplifier to drive over a wider band of frequencies within the required operational bandwidth with improved linearity. The transducer and matching network constitutes a full section 3'rd order band pass filter. This could also be done with other matching network designs that constitute a band pass filter of higher orders.

The transmitting part of the transducer arrangement 904 converts the broadband electrical waveform to mechanical vibrations. These mechanical vibrations cause a broadband acoustical signal to propagate from the transducer through the gaseous medium and to the pipe wall. At arrival at the pipe wall, the broadband acoustical signal is partly reflected from the wall and partly transmitted into the wall. If the partly transmitted broadband acoustical signal comprises components with wavelengths corresponding to twice the thickness of the pipe wall, or integral numbers of this value, these frequencies will create standing waves across the pipe wall.

When the emitted pulse comes to an end, resonant energy is reradiated and propagated thru the gaseous medium to be received at the receiving part of the transducer arrangement 904. The receiving part of the transducer converts mechanical vibrations to electrical signals normally in the order of mV. Due to loss in signal strength through the cable between the receiving part of the transducer arrangement 904 and the digitizer 906, these signals are applied to a low noise pre-amplifier 905 before sending it through the cable. This pre-amplifier and is usually located right after the hydrophone. If the cable is long and/or the amplitude of the signal is low, there could be a need of an additional amplifier before the signal is going into the digitizer 906.

The amplified electrical signal is digitized by a digitizer 906 such as an analogue to digital (A/D) converter and stored in either the memory of a processor or on a storage medium as e.g. a flash memory for later analysis. If the digitized data is stored in the memory of the processor, it could be analyzed, displayed and then stored. The processor is using a technique described below in further detail.

The control unit 907 comprises a processor and could also include a storage medium.

One possible improvement of the system is to use equalizing techniques on transmitting, receiving or both. The use of equalizing techniques can improve the overall phase linearity, efficiency and amplitude response of the system described in FIG. 9.

With Reference to the Algorithm

Figure 10:
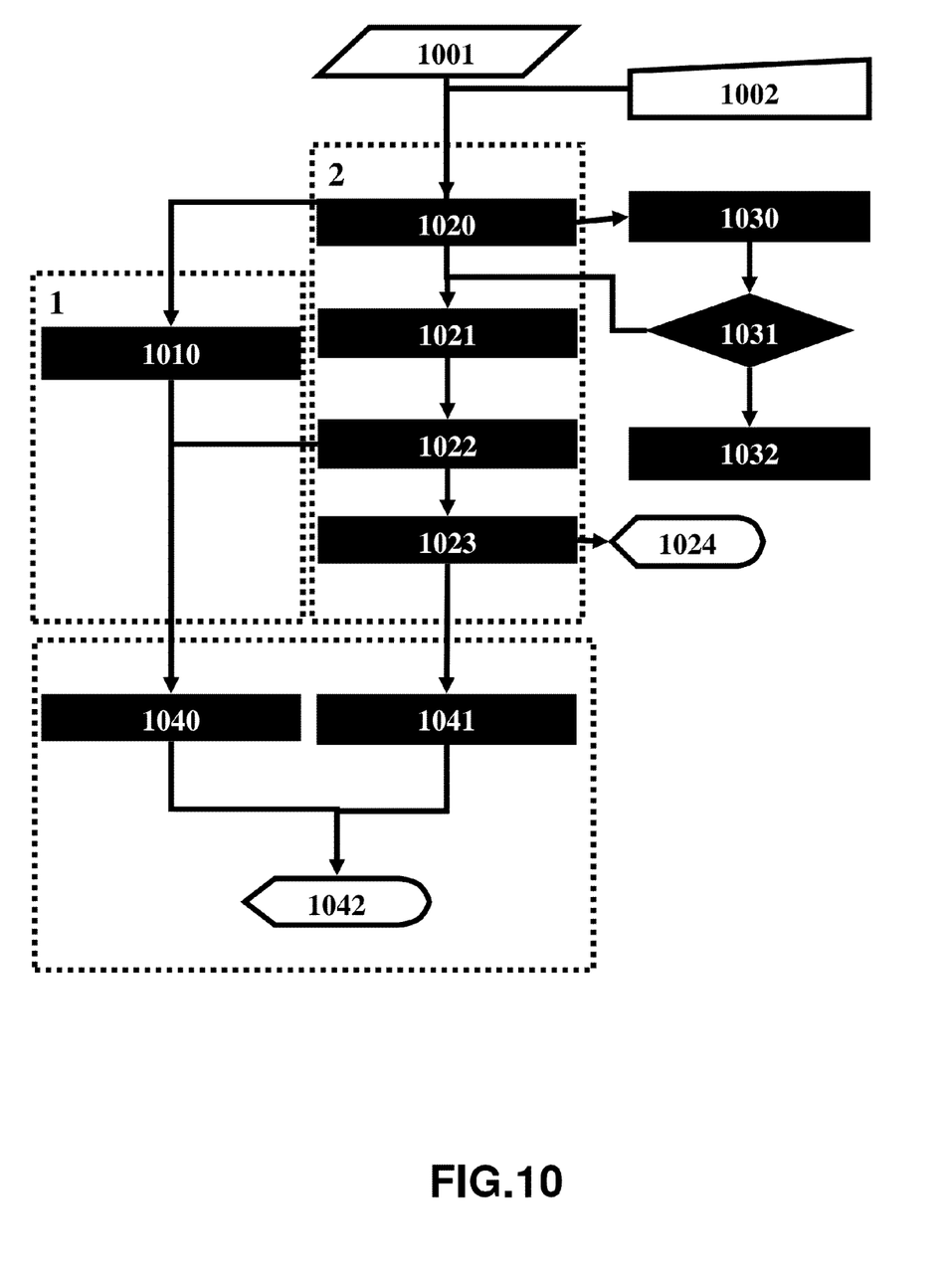
FIG. 10 is a schematic view of the algorithm of the invention.

Throughout the flow chart of FIG. 10 it is assumed that displayed data are also stored on a suitable storage medium.

1001 Time Signal

The series of real numbers corresponding to voltages from the DAQ unit 180. Henceforth it will be referred to as the time vector.

1002 Input Parameters

Speed of sound of measurement object, $c_o$

Length of time window for spectral estimation, N

Expected width of primary echo without resonance tail, W

Spectral estimation methods

Speed of sound of liquid, $c_w$

Choice of window functions (e.g. Hanning, Bartley)

Sampling frequency, $F_s$

Frequency interval used in transceiver

Expected upper thickness boundary

Minimum ratio between peak energies in primary and secondary echoes

Number of datasets in reference memory, M

Integer tolerance (1022-6)

Lower frequency weight threshold (1022-7)

1010 Time-Frequency Analysis

Inputs: time signal, spectral estimation technique, N, $F_s$

The power content in the time-frequency domain is estimated, using any standard technique, such as the sliding Fourier transform, or the Wigner distribution. The time of the maximum energy is identified, from this and N the start time of the tail is found.

Outputs: matrix of power, vector of times (in units of sampling interval), vector of frequencies (in Hz), start of tail time

1020 Identify Primary Echo

Inputs: time vector, expected width of primary echo

Finds the time corresponding to the largest pulse energy, and uses expected width of primary echo to find the start and stop of the echo.

Outputs: start and stop times of echo

1021 Spectral Estimation

Inputs: time vector, spectral estimation method, start and stop times for analysis, window functions, N, $F_s$ The frequency power content of the time signal is estimated using any standard technique, from periodogram based methods to parametric methods, for example using the Yule-Walker model. The estimation is performed in two windows, one comprising the tail only (starting at end of echo lasting to end of echo+N), and one comprising the echo and its tail, starting at the time start of echo−N lasting to end of echo+N.

Similarly, the bispectrum, the spectrum of the third-order cumulants, is computed using standard techniques. The interpretation of the bispectrum is less clear than for the ordinary spectrum, but its main advantages are to reject Gaussian noise efficiently and to highlight phase-coupled frequencies.

Outputs: power vector tail, vector with frequencies (in Hz) corresponding to the power values, power vector echo, vector with frequencies (in Hz) corresponding to the power values, bispectrum matrix, corresponding frequencies

1022 Identification of Resonance Frequencies
Inputs: frequency vector tail, frequency vector echo, frequency vector bispectrum, frequency interval used in transceiver Identifies harmonic frequencies and assigns the correct harmonic order to them. The procedure is detailed below under 1022-1 to 1022-8.
Outputs: index into time and frequency vectors corresponding to the resonance frequencies, harmonic orders
1023 Characterise Measurement Object
Inputs: $c_o$, resonance frequencies, harmonic orders The measurement object thickness is computed from $$d = \left\langle \frac{c_o n}{2 f_{res}} \right\rangle, \quad (2)$$

where n is the integer indicating the harmonic order, $f_{res}$ is the resonance frequency of harmonic order n, and $\langle \cdot \rangle$ denotes averaging.

Display results.
Outputs: thickness estimates
1030 Identify Secondary Echo
Inputs: time vector, start and stop times of primary echo, minimum ratio between peak energy of primary and secondary echoes The purpose is to determine whether there are two sets of echoes superimposed in the time signal, which indicates that there is a liquid layer between the transceiver and the measurement object. The secondary echo is the part of the original transmitted pulse from the transceiver which is transmitted through the gas-liquid interface, proceeds through the liquid, is reflected from the measurement object, and finally transmitted through the liquid-gas interface. Hence, the secondary echo contains the information from the measurement object and it is therefore crucial that the further analysis is performed on this echo rather than the primary echo.

The secondary echo is assumed to have a similar temporal extent as the primary echo, and to show up some time after the primary echo. If no secondary echo is found, empty values are returned.
Outputs: start and stop times of secondary echo
1031 Is Liquid Present?
Inputs: start and stop times of secondary echo If the inputs are empty, proceed the calculation with the primary echo determining the windows used for analysis.

If the inputs are non-empty, liquid is deemed to be present and the analysis proceeds using the secondary echo as the basis for determining relevant time windows.
Outputs: whether secondary echo was found
1032 The Depth of the Liquid Layer
Inputs: times of secondary and primary echoes, $c_W$ From the time difference between the secondary and primary echoes, the depth of the liquid layer is computed from $$l = \frac{c_W}{t_{sec} - t_{prim}}$$

with $t_{sec}$ and $t_{prim}$ being the time of arrival of the secondary and primary pulses, respectively.

Stores the value and displays it.
Outputs: estimated depth of liquid layer
1040 Decay Times
Inputs: time-frequency power matrix, indices of resonance frequencies, start of tail time The characteristic decay times of the resonance frequencies in the tail is found.
Outputs: the decay times of the resonance frequency
1041 Energy of Resonance Frequencies
Inputs: power vector tail, power vector echo, indices of resonance frequencies
Outputs: The ratio of the power in the resonance frequencies by the total power (power spectral density integrated with respect to frequency) in the echo pulse.

Figure 11:
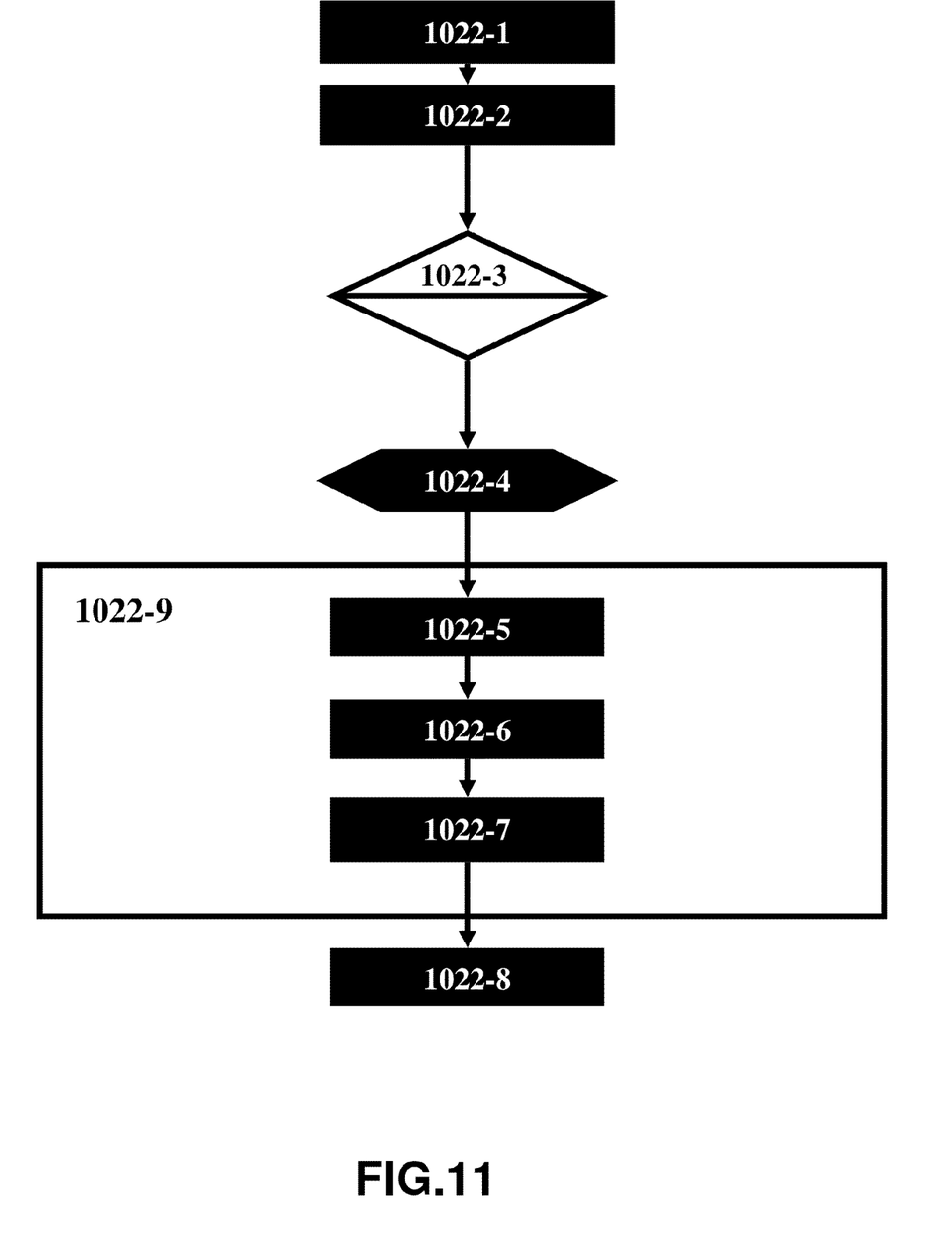
FIG. 11 is a flow chart for harmonic set identification.

Now, details of the flow chart of FIG. 11 for harmonic set identification is explained.
1022-1 Find Local Maxima/Minima
Inputs: power vector echo, power vector tail, bispectrum vector Finds local maxima in the bispectrum vector and the power vector tail. Finds local minima in the power vector echo.

The union of the three sets is the list of potential harmonic frequency candidates.
Outputs: harmonic frequency candidates
1022-2 Weighting of Maxima/Minima
Inputs: harmonic frequency candidates, power vector echo, power vector tail, bispectrum vector, filter size 1. Initialise weights vectors with values zero except at harmonic frequency candidates, where the value from the power vectors is used for bispectrum and tail. The weight vectors are normalised to the largest value in each case, e.g. all weights from the bispectrum candidate frequencies are normalised to the maximum value in the bispectrum vector.
2. subtract the power vector echo with its filtered version. The difference at the local minima defines the weight in this case. Normalise to the largest difference found.
3. One now has available three sets of weights, $W_{bisp}$, $W_{tail}$, $W_{echo}$, each normalised so the largest weight is 1.
4. For each set, scale the weights by $$W_j(i) = W_j(i) \prod_{k \neq j} \exp(-d_k)$$

where $d_k$ is the shortest distance to a non-zero weight in set k. $W_j(i)$ is the ith element of the jth set.
5. sum the weights from each set to obtain a single weight vector The ensuing weight vector gives weight to large peaks/deep minima in the respective power vectors, but penalises each weight if it is far from frequencies in the other sets. Weights are real numbers between 0 and 1.
Outputs: weights assigned to each harmonic frequency candidate
1022-3 Sort According to Weights
Inputs: weights, harmonic frequency candidates Sorts the weights vector, and uses the sort indices to rearrange the harmonic frequency candidates so that they are listed in decreasing weighted order.
Outputs: sorted harmonic frequency candidates
1022-4 Build Frequency Sets
Inputs: sorted harmonic frequency candidates, weights, frequency weights threshold 1. Reject all candidate frequencies below the threshold
2. Rearrange frequency candidates into sets. If there are N candidates, then build N lists $\{f_1, \ldots, f_N\}$, $\{f_1, \ldots, f_{N-1}\}$, and so on, where the smallest weighted frequency in the previous list is progressively removed. Each list is henceforth known as a frequency set.

Each frequency set is denoted $F_n$.
Outputs: frequency sets $\{F_1, F_2, \ldots, F_N\}$
1022-5 Loop Through all Sets, i=1, ..., N
1022-6 Find Harmonic Sets:
Input: Frequency sets $\{F_1, F_2, \ldots, F_N\}$, integer tolerance, expected maximum thickness, frequency interval used in transceiver The harmonic sets for one frequency list $F_i$ is computed as follows: initially a n×n matrix with filled with all possible ratios of frequencies is found, $$M'_{ij} = \frac{f_i}{f_j}$$

The matrix M' is used to build a larger matrix M by concatenating kM', k=1, 2, ..., $k_{max}$ as follows:

$$M = \begin{bmatrix} 1 \cdot M' \\ \vdots \\ k_{max} \cdot M' \end{bmatrix}$$

The integer $k_{max}$ is computed from the maximum allowed thickness, a user input.

The next step is to round all elements in M to their nearest integer, and compare the difference between the integer values and the frequency ratios in M. An element is deemed an integer if this difference is less than a user specified threshold, typically 0.1, and a matrix N where all non-integer elements in M equal zero if found. The rows in N identify the harmonic sets: for a given $N_{ij}$ element the value corresponds to the harmonic order of frequency $f_j$ in the frequency list.
Output: Set of integer matrices $\{N_1, N_2, \ldots, N_N\}$.
1022-7 Removing Elements in $N_n$:
Input: Set of integer matrices $\{N_1, N_2, \ldots, N_n\}$, expected maximum thickness, frequency interval used in transceiver The harmonic order matrices $N_n$ are significantly reduced by removing rows containing a value above the max order $k_{max}$. All duplicate rows are removed, and rows giving a thickness above the user input maximum value are removed.
Outputs: Set of reduced integer matrices $\{N_1, N_2, \ldots, N_n\}$.
1022-8 Count Number of Harmonics in $N_i$:
Input: Set of reduced integer matrices $\{N_1, N_2, \ldots, N_n\}$.

For each $N_n$, the harmonic set with the largest number of unique frequencies are recorded. The numbers are stored in a vector $\Phi$.
Output: Vector $\Phi$ of maximum number of unique sets.
1022-9 Finding Optimum Subset of Frequencies:
Input: Vector $\Phi$ of maximum number of unique sets, number of frequencies in each frequency set, set of reduced integer matrices $\{N_1, N_2, \ldots, N_n\}$.

The aim is to find the optimum subset of the original frequency list. Each subset is associated with a number of unique harmonics stored in $\Phi$. In addition, each subset has a number of frequencies.

The optimal subset if found by finding the highest ratio of $\Phi$ divided by the number of frequencies in the list, neglecting the trivial case for only a single frequency. In this process we have accomplished both a rejection of frequencies, and obtained harmonic sets.
Output: Indices to optimal subset of frequencies, set of harmonics.

OTHER APPLICATIONS

So far the system of invention has been described as a pipe scanner, but the system of invention could also be applied as a hand held device in air. For this purpose the device could contain a single transducer system if the application mode is spot checks. For scanning purposes an array would most likely be appropriate. The application areas could be spot checks/scanning of ship hulls from the inside or onshore pipes and storage tanks from the outside. Instead of applying the system of invention for thickness scanning of pipe walls or containers, the same system will be applicable for characterizing pipe walls if the thickness and sound velocity of these walls are known. This characterization could be to detect deviations from a perfect pipe wall. One example would be inside characterization scanning of risers. Another application will be well logging/down-hole inspection during production. The casing thickness will be measured, as well as characterization of the medium outside the casing, e.g. differentiate between concrete gas or fluid.

REFERENCES

International Publication Number: WO 01/83122 A1—Method and apparatus for equalising transfer functions of linear electro-acoustic systems.

What is claimed is:
1. Method for operating an electroacoustic device configured to operate in a gas filled space and from a first side of an object to be measured for making a non-contact ultrasonic thickness measurement of said object or for making a non-contact ultrasonic characterization of a medium located on an opposite side of said object,
the method including providing said device comprising an electro acoustic transducer device, an electronic transceiver device connected to the electro acoustic transducer device and being configured to excite the electroacoustic transducer device to emit an acoustic signal towards said object and to receive an acoustic response signal therefrom, and a signal processor configured to process the response signal and to determine on basis of the acoustic response signal the thickness characteristic of said object to be measured, the electroacoustic transducer device having an acoustic transducer-to-gas interface, and providing the transceiver device being configured to drive the electroacoustic transducer device to emit into a gas filled space between the electroacoustic transducer device and said object to be measured an acoustic broadband pulse towards said object and to receive an acoustic resonance response signal in the acoustic response signal at a level allowing acquisition of the resonance response signal above a predetermined signal/noise level, the method further comprising:
outputting from the transceiver said received acoustic response signal as a digitized time vector of a series of real numbers corresponding to voltages being output from the transducer device and representing the acoustic response signal,
providing said signal processor with an input for said time vector and an input for input parameters,
performing in the signal processor a time frequency analysis on basis of the time vector for identifying the time of the maximum energy and from this and a length of time window for spectral estimation determining the start time of the resonance tail, and a matrix of power, a vector of times, and a vector of frequencies, and
to generate a thickness estimate on basis of the vector of time, input parameters and an output from the time frequency analyses, by preforming in the signal processor the steps of:

a) identification of primary echo,
b) spectral estimation by estimating frequency power contents of the time signal,
c) identification of resonance frequency by identification of harmonic frequencies and assigning the correct harmonic order to them, and
d) characterization of the object by computing object thickness on basis of the speed of sound in said object, the integer indicating the harmonic order, and the resonance frequency of the harmonic order, and averaging.

2. The method of claim 1, wherein the step of identification of primary echo comprises determining the point in time corresponding to the largest pulse energy, and using expected width of primary echo to determine start and stop of the echo, with time vector and the expected widths of the primary echo as inputs, and
outputting the start and stop times of echo.

3. The method of claim 1, wherein the step of spectral estimation includes estimating the frequency power content of the time vector, with time vector, spectral estimation method, start and stop times for analysis, windowing function, duration of time window for spectral estimation, N, and sampling frequency, $F_s$, as inputs, using a standard technique, from periodogram based methods to parametric methods, such as for example using the Yule-Walker-model, which estimation is performed in two windows, one window comprising the tail only, starting at end of echo and lasting to end of echo+N, and one comprising the echo and its tail, starting at the time of start of echo−N and lasting to end of echo+N, and wherein bispectrum, the spectrum of the third order cumulants, is correspondingly computed using standard techniques, wherein interpretation of this bispectrum is less clear than for the ordinary spectrum, while its main advantages are to reject Gaussian noise efficiently and to emphasize phase coupled frequencies, and
outputting power vector of tail, and vector of frequencies corresponding to power values, power vector of echo, a vector of frequencies corresponding to the power values, bispectrum matrix, and corresponding frequencies.

4. The method of claim 1, wherein identification of resonance frequencies comprises identifying harmonic frequencies and assigning the correct harmonic order to them, with frequencies vector of tail, frequencies vector of echo, frequencies vector of bispectrum, and frequency interval used in the transceiver as inputs, and
outputting index into time and frequency vectors corresponding to the resonance frequencies, harmonic orders.

5. The method of claim 4, wherein the method further comprises finding local maxima in the bispectrum vector and the power vector of tail, and finding local minima in the power vector of echo, wherein a union of the three sets is the list of potential harmonic frequency candidates, with the power vector of echo, power vector of tail, and bispectrum vector as inputs, and
outputting harmonic frequency candidates.

6. The method of claim 5, wherein the method further comprises weighting of maxima/minima with harmonic frequency candidate, power vector of echo, power vector of tail, bispectrum vector, and filter size as inputs, by
a) initializing weights vectors with values zero except at harmonic frequency candidates, where the value from power vectors is used for bispectrum and tail, wherein the weight vectors are normalized to the largest value in each case, for example all weights from bispectrum candidate frequencies are normalized to the maximum value in the bispectrum vector, and
b) subtracting power vector of echo with its filtered version, the difference at the local minima defining the weight in this case, and normalizing to the largest difference found,
c) making available three sets of weights, bispectrum weights $W_{bisp}$, tail weights $W_{tail}$, echo weights $W_{echo}$, each normalized such that the largest weight is 1,
d) for each set, scaling the weights by $$W_j(i) = W_j(i) \prod_{k \neq j} \exp(-d_k)$$

where $d_k$ is the shortest distance to a none-zero weight in set k, and the weight $W_j(i)$ is the i'th element in the j'th set, and
e) summing the weights from each set to obtain a single weight vector, wherein the ensuing weight vector gives weight to large peaks/deep minima in the respective power vectors, but penalizes each weight if it is far from frequencies in the other sets, and wherein the weights are real numbers between 0 and 1, and
f) outputting weights assigned to each harmonic frequency candidate.

7. The method of claim 6, wherein the method further comprises sorting according to weights, with weights and harmonic frequency candidates as inputs, by sorting the weights vector, and using the sort indices to rearrange the harmonic frequency candidates such that they are listed in decreasing weighted order, and
outputting sorted harmonic frequency candidates.

8. The method of claim 7, wherein the method further comprises building frequency sets, with sorted harmonic frequency candidates, weights, and a frequency weight threshold as inputs, by
a) rejecting all candidate frequencies below the threshold, and
b) rearranging frequency candidates into set, wherein, if there are N candidates, then building N lists $\{f_1, \ldots, f_N\}$, $\{f_1, \ldots, f_{N-1}\}$, and so on, where the smallest weighted frequency in the previous list is progressively removed, and each list is henceforth known as a frequency set, each frequency thereof denoted $F_n$, and
outputting the frequency set $\{F_1, F_2, \ldots, F_N\}$.

9. The method of claim 8, wherein the method further comprises finding an optimal set of frequencies as the optimal subset of the original frequency list, with the vector for maximum number of unique set, number of frequencies in each frequency set, and set of reduced integer matrixes $\{N_1, N_2, \ldots, N_n\}$ as inputs, wherein the optimal subset is found by finding the highest ratio of divided by number of frequencies in the list, while this regarding the trivial case for only one single frequency, whereby is achieved both a rejection of frequencies, and an obtained harmonic set, and
outputting indexes to optimal subsets of frequencies, and sets of harmonics.

10. The method of claim 9, wherein the method further comprises counting number of harmonics in $N_i$, with set of reduced integer matrixes $\{N_1, N_2, \ldots, N_n\}$ as input, wherein for each $N_n$, the harmonic sets with the largest number of frequencies are recorded, and the number is stored in a vector, and
outputting vector of maximum number of unique sets.

11. The method of claim 9, wherein building a set of frequencies comprises looping through all sets, i=1, ..., N.

12. The method of claim 11, wherein the method further comprises finding the harmonic set, with the frequency set $\{F_1, F_2, \ldots, F_N\}$, integer tolerance, expected maximum thickness, and frequency interval used in transceiver as input, wherein the harmonic sets for a frequency list $F_i$ are computed as follows:
initially a n×n matrix filled with all possible ratios of frequencies is found, $$M'_{ij} = \frac{f_i}{f_j}$$

matrix M' is used to build a larger matrix M by concatenating kM', k=1, 2, ..., $k_{max}$ as follows:

$$M = \begin{bmatrix} 1 \cdot M' \\ \vdots \\ k_{maks} \cdot M' \end{bmatrix}$$

where the integer $k_{max}$ is computed from the maximum allowed thickness, a user input, and the next step is to round all elements in M to their nearest integer, and comparing the difference between the integer values and the frequency ratios in M, where an element is deemed an integer if its difference is less than a user specified threshold, typically 0,1, and a matrix N where all non-integer elements in M equal to zero are found, and where the rows in N identifies the harmonic sets, for a given $N_{ij}$ element the value corresponds to the harmonic order of frequency $f_j$ in the frequency list, and outputting a set of integer matrixes $\{N_1, N_2, \ldots, N_N\}$.

13. The method of claim 12, wherein the method further comprises removing elements in $N_n$, whereby harmonic order matrixes $N_n$ are significant reduced by removing rows containing a value above the max order $k_{max}$, with a set of integer matrixes $\{N_1, N_2, \ldots, N_n\}$, expected maximum thickness, and frequency interval used in transceiver as inputs, whereby all duplicate rows are removed, and rows giving a thickness above the user input maximum value are removed, and
outputting a set of reduced integer matrixes $\{N_1, N_2, \ldots, N_n\}$.

14. The method of claim 1, wherein characterization of said object comprises computing the object thickness from $$d = \left\langle \frac{c_0 n}{2 f_{res}} \right\rangle,$$

wherein $c_0$ is the speed of sound in said object, n is an integer indicating the harmonic order, $f_{res}$ is the resonance frequency of the harmonic order n, and <•> indicates averaging, with $c_0$, resonance frequencies, and harmonic orders as inputs, and outputting thickness estimates.

15. The method of claim 1, wherein said method further comprises identification of secondary echo to determine whether two sets of echos are superimposed in the time signal, which indicates that a layer of liquid is present between the transceiver and said object, which secondary echo is part of the originally emitted pulse from the transceiver that is transmitted to the gas-liquid-interface, and further through said liquid being reflected from said object, and finally transferred to the liquid-gas-interface, which secondary echo is assumed to have a temporal extent similar to that of the primary echo and to sjow up delayed with respect to the primary echo, and which secondary echo contains information from the object, and wherein the further analysis is made on basis of this echo instead of the primary echo, with time vector, start and stop times of the primary echo, and the minimum ratio of peak energy of the primary and secondary echos as inputs, and
outputting the start and stop times of the secondary echo, and returning empty values if no secondary echo is found.

16. The method of claim 15, further comprising determining whether liquid is present, with start and stop times of the secondary echo as input, and if said inputs are empty, continuing estimation with the primary echo for determining windows used for analysis, and if inputs are not empty, liquid is assumed to be present and the analysis proceeds using the secondary echo as basis for determining relevant time windows, and outputting whether or not the secondary echo was found.

17. The method of claim 16, said method further comprising determining a depth of the liquid layer, with times of said secondary and primary echos, and the velocity of sound $c_w$ in liquid as inputs, from the time difference between the secondary and primary echos, wherein the depth of the liquid layer is computed by $$l = \frac{c_w}{t_{sek} - t_{prim}}$$

with $t_{sek}$ and $t_{prim}$ being the time of arrival of the secondary pulse and the primary pulse, respectively, and
outputting estimated depth of liquid layer.

18. The method of claim 1, further comprising determining the characteristic decay times for resonance frequencies in the tail, with time frequency power matrix, indices of resonance frequencies, and time of start of tail as inputs, and
outputting decay times of resonance frequency.

19. The method of claim 1, wherein the method further comprises determining energy of resonance frequencies, with power vector of tail, power vector of echo, and indices of resonance frequencies as inputs, and
outputting the ratio of the power in the resonance frequencies to the total power in the echo pulse.

20. An electroacoustic apparatus configured to operate in a gas filled space and from the first side of an object to be measured for making a non-contact ultrasonic thickness measurement of said object to be measured or for making a non-contact ultrasonic characterization of a medium located on an opposite side of said object to be measured, which apparatus comprises an electroacoustic transducer device, an electronic transceiver device connected to the electroacoustic transducer device and being configured to excite the electroacoustic transducer device to emit an acoustic signal towards said object to be measured and to receive an acoustic response signal therefrom, and a single processor adapted to a processing the response signal and to determine on basis of the acoustic response signal a thickness characteristic of said object to measured, wherein the electroacoustic transducer device having an acoustic transducer-to-gas interface, said transducer device being adapted to drive the electroacoustic transducer device for emitting into a gas filled space between the electroacoustic transducer device and said object to be measured and acoustic broad bounded pulse towards said object and to receive an acoustic resonance response signal in the acoustic response signal at a level allowing acquisition of the resonance response signal above a predetermined signal/noise level, and to output the received acoustic response signal as a digitized time vector of a series of real numbers corresponding to voltages being output from the transducer device and representing the acoustic response signal, the signal processor having an input for the time vector and an input for input parameters, and the signal processor being configured to make a time frequency analysis on basis of the time vector for identifying the time of the maximum energy and from this a length of time window for spectral estimation, finding the start time of the resonance tail, a power matrix, a time vector and a frequency vector (in Hz), and to provide a thickness estimate on basis of the time vector and a spectrum estimation technique, a duration of time window for spectrum estimation, and a sampling frequency, the signal processor being configured to preform the steps of a) identification of primary echo,
b) a spectral estimation by estimating frequency power contents of the time signal,
c) identification of resonance frequencies by identifying harmonic frequencies and assigning the correct harmonic order to them, and
d) characterizing of said object by computing an object thickness on basis of the speed of sound in said object, the integer indicating harmonic order, and the resonance frequency of the harmonic order, and averaging.

21. The apparatus of claim 20, wherein the transceiver device connected to the electroacoustic transducer device being configured to operate with acoustic signals having acoustic components in a frequency arrange being at least one decade lower than frequencies used in time of flight measurements in said object to be measured.

22. The apparatus of claim 20, including a transducer carrier device being configured to maintain the gas filled space between the transducer and said object to a predetermined distance from a surface of said object that faces the gas filled space.

23. The apparatus of claim 22, wherein the transducer carrier device being configured to convey the electroacoustic transducer along a surface of said object facing the gas filled space.

24. The apparatus of claim 20, wherein said parameters comprising the acoustic response signal, a velocity of sound in said object, duration of a time window for spectral estimation, an expected width of primary echo without resonance tail, spectral estimation methods, a speed of sound in liquid, a selection of window functions, a sampling frequency, a frequency interval used in transceiver for an expected upper thickness limit, a minimum ratio between top energies in primary and secondary echos, a number of data sets in reference memory, integer tolerances, and a lower frequency threshold.

* * * * *